Figure 1:
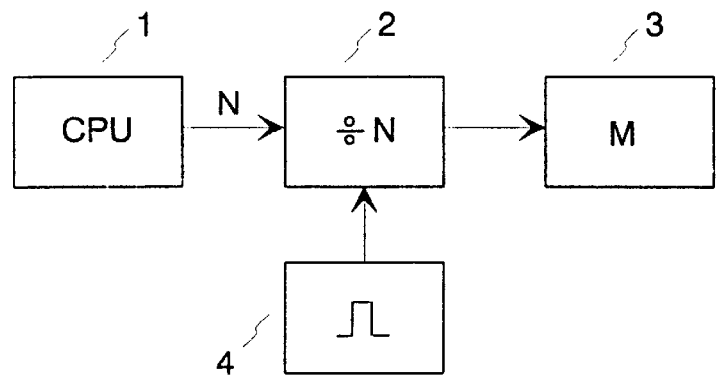

United States Patent [19]
Wahlström

[11] Patent Number: 5,903,126
[45] Date of Patent: May 11, 1999

[54] CONTROL OF STEPPER MOTOR

[75] Inventor: Matti Wahlström, Helsinki, Finland

[73] Assignee: Orion-Yhtyma Oy, Helsinki, Finland

[21] Appl. No.: 08/569,431

[22] Filed: Dec. 8, 1995

[30] Foreign Application Priority Data

Dec. 9, 1994 [FI] Finland ..................... 945796

[51] Int. Cl.⁶ ..................................................... H02P 8/00
[52] U.S. Cl. ........................................... 318/696; 318/685
[58] Field of Search ..................... 318/685, 696

[56] References Cited

U.S. PATENT DOCUMENTS

| | | | |
|---|---|---|---|
| 3,719,878 | 3/1973 | Ferguson et al. | 318/565 |
| 4,349,771 | 9/1982 | Buxton | 318/685 |
| 4,420,717 | 12/1983 | Wallace et al. | 318/696 |
| 4,587,473 | 5/1986 | Turvey | 318/696 |
| 4,929,879 | 5/1990 | Wright et al. | 318/696 |

Primary Examiner—William M. Shoop, Jr.
Assistant Examiner—Kim Lockett
Attorney, Agent, or Firm—Howard L. Rose

[57] ABSTRACT

The present invention relates to a method and a circuit arrangement for controlling a stepper motor, e.g. in a panoramic X-ray apparatus. In the method of the invention, the control data of a processor (5) is first converted into an analog signal with a digital-analog converter (6), and the signal thus obtained is integrated with an integrating circuit (7,10), whereafter the signal is converted into pulses controlling the stepper motor (9) with a voltage-frequency converter (8). The circuit arrangement comprises preferably one or two integrators. In consequence, the changes in the speed of rotation of the stepper motor can be made stepless, whereby the stresses directed at the mobile parts are small, and mechanical oscillation caused by high momentary forces is avoided. In addition, the loading of the processor can be made uniform. Error correction circuits employing feedback are employed to enhance operation of the invention.

12 Claims, 1 Drawing Sheet

CONTROL OF STEPPER MOTOR

The present invention relates to a method and an arrangement for controlling a stepper motor, for instance in panoramic X-ray apparatus.

Conventionally, the stepper motors are controlled by converting the digital control data of the processor into control pulses of the stepper motor with the aid of an oscillator and the divider to be programmed. Thereby, the speed of rotation of the stepper motor is inversely proportional to the digit transmitted by the processor to the divider to be programmed.

A drawback related to circuit designs known in the art is that when the processor is changing the control frequency of the stepper motor, the change takes place in jumps, whereby monitoring the control causes great momentary inertial forces in the motor and the apparatus connected thereto. Depending on the mechanical structure of the equipment, said forces may cause further problems e.g. mechanical oscillation. In panoramic X-ray apparatus, stepper motors are used, for instance, in the course of the photographing for moving the X-ray source and the film, whereby the quality of the photographing result is deteriorated by the mechanical oscillation.

Great inertial forces require great power in the stepper motor, to be enabled to monitor the effect of the control. Therefore, both the power of the motor and the mechanical strength related to the motor have to be overdimensioned.

In prior art methods, the processor is, while accelerating the stepper motor, required to update continuously the control data, which requires large capacity of the processor, but at constant speed, the processor is not loaded. In addition, the same processor is frequently used for controlling a number of stepper motors, the acceleration and standard speed periods of which may overlap. Thus, the loading of a processor varies greatly and it is necessary to dimension its capacity on the basis of a momentary loading situation in which the speeds of rotation of a number of stepper motors change simultaneously. On the other hand, if the updating frequency of the control data is too small because of the small capacity of the processor, the jumps in the speed changes of the stepper motor may be particularly great.

The object of the present invention is to create a procedure and a circuit arrangement for controlling a stepper motor, in which the drawbacks mentioned above have been corrected. The procedure of the invention is characterized in what is presented in the characteristic features' part of claim 1, and the circuit arrangement of the invention is characterized in what is presented in the characteristic features' part of claim 7. Advantageous embodiments of the invention are presented in the dependent claims.

The invention is described below with the aid of a drawing in which

Figure 2:
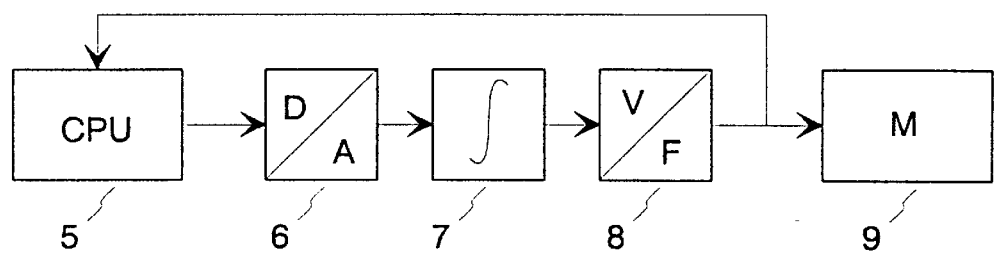
Figure 3:
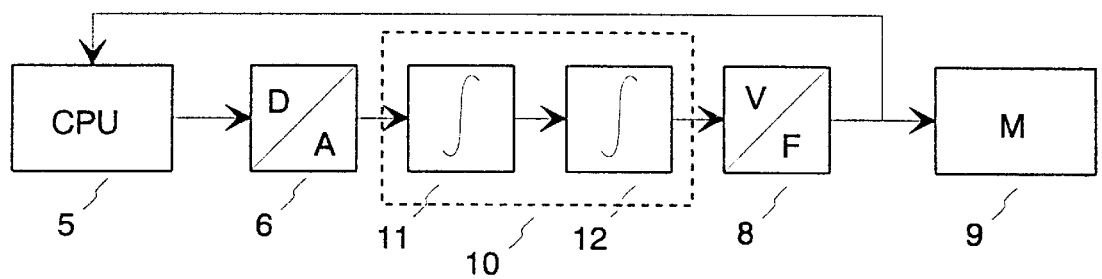

FIG. 1 presents a conventional way of controlling a stepper motor,

FIG. 2 presents a circuit arrangement of the invention for controlling the stepper motor, FIG. 3 presents an alternative circuit arrangement of the invention, in which the integrating circuit comprises two integrators.

FIG. 1 presents schematically a prior art circuit design, in which a stepper motor is controlled with a processor and which is here generally described at the beginning. Therein, a signal of constant frequency is received from an oscillator 4 and connected to the input of a programmable divider 2. From the out-put of the divider, pulses are provided for a stepper motor 3 (M), the frequency thereof being the frequency of the oscillator divided by digit N, in which digit N is derived from the processor 1 (CPU) in digital form. For instance, in a panoramic X-ray apparatus, the control data of the stepper motors according to the photographic process have been stored in the memory of the apparatus (not shown in the figure). When changing the speed of rotation of the stepper motor, the processor supplies changing digits to the programmable divider. Thereby, the control frequency of the stepper motor changes in jumps, and the magnitude of the momentary frequency changes is dependent on the resolution of the processor and the divider being programmed, and on the ability of the processor to update control data at brief intervals. Particularly great the momentary changes are at high speeds of rotation of the stepper motor, whereby changing a value of divider N in one unit causes a great change in the control frequency. As mentioned above, changing the control frequency in jumps may cause problems in practice.

FIG. 2 presents a circuit arrangement according to the present invention with which changes in the speed of rotation can be made to take place steplessly. Processor 5 (CPU) provides digital control data to a digital-analog converter 6 (D/A) which converts it into an analog signal. The analog signal is integrated in integrator 7 and conducted into a voltage-frequency converter 8 (V/F). From the output of the converter the control pulses can be provided for the stepper motor 9 (M), their frequency being directly proportional to the amplitude of the analog signal derived from the integrator. Thus, the rotational acceleration of the stepper motor can be made directly proportional to the control data provided by the processor. Therefore, thanks to the integrating circuit, the discrete control changes from the processor cause no frequency changes in jumps in the control signal of the stepper motor.

Since the control data of the processor is converted into an analog signal, inaccuracies occur in the signal path. To be able to control a stepper motor with adequate precision, the control signal of the stepper motor has been fedback to the processor. In this manner, the processor is capable of monitoring the actual movement of the stepper motor and, if needed, of making corrections in the control data. Another alternative is to feedback an output signal of the integrator to the processor which is first converted to digital with an analog-digital converter (not shown in the figure).

FIG. 3 shows an alternative circuit arrangement of the present invention in which an integrating circuit 10 comprises two integrators 11,12. Thereby, the time derivative of the rotation acceleration is directly proportional to the control data provided by the processor. Thanks to said arrangement, acceleration changes of the stepper motors can be made stepless, and hence, no changes of step impulse type occur in the inertia forces. In other respects, the circuit arrangement is equivalent to the circuit arrangement presented in FIG. 2.

Thanks to the circuit arrangement of the invention, the peak value of the forces directed at the stepper motor and the apparatus in association therewith can be made small. Therefore, less powerful stepper motors and less heavy mechanical support structures can be used, or alternatively, greater loads can be moved at conventional motor powers. In addition, mechanical oscillations caused by step-type impulses can be avoided, because of which e.g. a better photographic result can be obtained qualitatively with a panoramic X-ray apparatus.

Moreover, with a circuit arrangement of the invention, loading a processor can be stabilized essentially because when the speed of rotation is changed, a need to update the processor control is smaller. When using constant accelerations in stepper motor speed changes, a very uniform loading can be obtained even in using one integrator only. If the change speed of acceleration is made constant, a more uniform loading can be achieved by the use of two integrators.

In the exemplary applications described above, one or two integrators have been used for integrating the analog signal. It goes without saying that in a circuit arrangement according to the present invention, more integrators may be used. In a practical implementation, integration of several order can be accomplished with one circuit arrangement, instead of separate integrators.

In the circuit arrangements presented here a conventional linear converter is used as the digital-analog converter. Similarly, converting an analog signal into pulses controlling the stepper motor has been carried out with a linear voltage-frequency converter. However, for accomplishing said conversions also converters of other type may be used.

The components included in the circuit arrangement can be implemented using conventional technique. Their detailed dimensioning is not presented in the present context in greater detail because they are assumed to belong to the standard skills of a person skilled in the art which he may apply after reading through the present description.

Some applications of the circuit arrangement according to the present invention are presented above. The principle according to the invention may be modified within the protective scope of the claims, e.g. regarding the structural details and areas of application.

I claim:

1. A method for controlling a stepper motor with a processor, characterized in that digital data produced by the processor is converted into an analog signal, integrating the analog signal at least once to produce a control signal for the stepper motor, converting the integrated signal into a further signal having a frequency for controlling the stepper motor, and employing the further signal to control the stepper motor.

2. Method according to claim 1, characterized in that integration of a first order is performed for the analog signal in order to change the speed of rotation of the stepper motor steplessly.

3. Method according to claim 1, characterized in that integration of second order is performed for the analog signal in order to change the speed of rotation and the rotation acceleration of the stepper motor steplessly.

4. A method according to claim 1 characterized in that the analog signal is converted into a plurality of pulses for controlling the stepper motor with voltage-frequency conversion.

5. A Method according to claim 1 characterized in that the stepper motor is used for moving X-ray source or an X-ray film of a panoramic X-ray apparatus in a photographic process.

6. A circuit arrangement for controlling a stepper motor characterized in that the arrangement comprises, a processor for producing digitized control data for controlling the stepper motor, a digital-analog converter (6) to convert said control data derived from the processor into an analog signal a circuit (7,10) for integrating the analog signal to produce a signal for controlling the stepper motor and a second converter (8) to convert the amplitude of the integrated analog signal into a signal having a frequency for controlling the stepper motor, and means for applying the further signal to said stepper motor.

7. A circuit arrangement according to claim 6, characterized in that said integrating circuit (7) comprises one integrator for changing the speed of rotation of the stepper motor steplessly.

8. A circuit arrangement according to claim 6, characterized in that the integrating circuit (10) comprises two series connected integrators (11,12) for changing the speed of rotation and the rotation acceleration of the stepper motor steplessly.

9. A circuit arrangement according to claim 6 or claim 7 or claim 8, characterized in that said second converter (8) is a voltage-frequency converter.

10. A circuit arrangement according to claim 6 or claim 7 or claim 8 or claim 9, characterizedized in that the signal after the second converter, or a signal comparable thereto, has been fed back to the processor to compensate for the errors in controlling the stepper motor.

11. A circuit arrangement according to claim 6 or claim 7 or claim 8 or claim 9 or claim 10, characterized in that the circuit arrangement is part of a panoramic X-ray apparatus in which an X-ray source or any X-ray film cassette has been coupled to the stepper motors for controlling their movements.

12. A method according to claim 1 characterized by comparing the signal applied to the stepper motor with the signal from which the control signal is derived, and correcting the control signal when an error is detected.

* * * * *